United States Patent
Knoepfle et al.

(10) Patent No.: US 9,427,275 B2
(45) Date of Patent: Aug. 30, 2016

(54) BENDING INSTRUMENT FOR A SURGICAL ELEMENT

(71) Applicant: Stryker Leibinger GmbH & Co. KG, Freiburg (DE)

(72) Inventors: Christian Knoepfle, Donaueschingen (DE); Karl Greiner, Muehlheim (DE); Manfred Schmuck, Meuhlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 299 days.

(21) Appl. No.: 14/273,053

(22) Filed: May 8, 2014

(65) Prior Publication Data

US 2014/0364860 A1 Dec. 11, 2014

(30) Foreign Application Priority Data

Jun. 6, 2013 (EP) .................................... 13002919

(51) Int. Cl.
*A61B 17/88* (2006.01)
*B21D 7/06* (2006.01)

(52) U.S. Cl.
CPC ............. *A61B 17/8863* (2013.01); *B21D 7/06* (2013.01); *B21D 7/063* (2013.01)

(58) Field of Classification Search
CPC ..... A61B 17/8863; B21D 7/06; B21D 7/063
See application file for complete search history.

(56) References Cited

U.S. PATENT DOCUMENTS

| | | | |
|---|---|---|---|
| 275,881 A | 4/1883 | Brastow et al. | |
| 2,252,891 A | 8/1941 | Heinrich | |
| 3,244,201 A | 4/1966 | Wallshein | |
| 3,597,775 A * | 8/1971 | McCasland | A01K 95/02 7/106 |
| 3,626,995 A * | 12/1971 | Keenan | H05K 13/023 140/106 |
| 3,956,950 A * | 5/1976 | Jamell | B21F 1/06 140/104 |
| 4,005,593 A | 2/1977 | Goldberg | |
| 4,474,046 A | 10/1984 | Cook | |
| 4,488,425 A | 12/1984 | Meikle | |
| 5,113,685 A | 5/1992 | Asher et al. | |
| 5,490,409 A | 2/1996 | Weber | |

(Continued)

FOREIGN PATENT DOCUMENTS

| | | |
|---|---|---|
| DE | 172419 C | 6/1906 |
| DE | 276067 C | 7/1914 |

(Continued)

OTHER PUBLICATIONS

European Search Report, EP 13002919, dated Dec. 9, 2013.

*Primary Examiner* — Andrew Yang
(74) *Attorney, Agent, or Firm* — Lerner, David, Littenberg, Krumholz & Mentlik, LLP

(57) ABSTRACT

A bending instrument for a surgical element has two branches or arms which are pivotable relative to one another. A bending punch and two counter members are provided. The counter members interact with the bending punch to deform the surgical element. An actuator for the bending punch is adapted to convert an actuating movement of the branches or arms into a linear movement of the bending punch in a direction towards a region between the two counter members in order to bend the surgical element therebetween. First and second bending structures are provided for co-operatively bending the surgical element, wherein the bending instrument is configured to convert an actuating movement of the branches into a mating movement of the first and second bending structures towards one another.

20 Claims, 2 Drawing Sheets

(56) References Cited

U.S. PATENT DOCUMENTS

| | | |
|---|---|---|
| 5,564,302 A | 10/1996 | Watrous |
| 5,572,899 A | 11/1996 | Balaity et al. |
| 5,651,283 A | 7/1997 | Runciman et al. |
| 6,644,087 B1 | 11/2003 | Ralph et al. |
| 7,454,939 B2 | 11/2008 | Garner et al. |
| 7,473,257 B2 | 1/2009 | Knopfle et al. |
| 7,488,331 B2 | 2/2009 | Abdelgany |
| 7,740,634 B2 | 6/2010 | Orbay et al. |
| 8,491,601 B2 | 7/2013 | Schmuck et al. |
| 9,186,195 B2* | 11/2015 | Petit .................. B21D 7/063 |
| 9,254,158 B2* | 2/2016 | Koch ................. A61B 17/8071 |
| 2006/0259072 A1* | 11/2006 | Di Emidio ......... A61B 17/8863 606/205 |
| 2009/0222020 A1 | 9/2009 | Schmuck et al. |
| 2010/0268119 A1* | 10/2010 | Morrison ............ A61B 17/7091 600/587 |
| 2012/0047980 A1* | 3/2012 | Harper ................. B21D 7/063 72/199 |
| 2012/0247173 A1 | 10/2012 | Paris et al. |
| 2015/0012003 A1* | 1/2015 | Ryan .................. A61B 17/8863 606/101 |

FOREIGN PATENT DOCUMENTS

| | | |
|---|---|---|
| DE | 1087990 B | 8/1960 |
| DE | 1914120 U | 4/1965 |
| DE | 2850892 A1 | 5/1980 |
| DE | 10301692 A1 | 8/2004 |
| EP | 1721706 A1 | 11/2006 |
| JP | 54034499 U | 3/1979 |
| JP | 2003500154 A | 1/2003 |
| JP | 2003102743 A | 4/2003 |
| JP | 2007185535 A | 7/2007 |
| WO | 2006047581 A2 | 5/2006 |

\* cited by examiner

BENDING INSTRUMENT FOR A SURGICAL ELEMENT

CROSS-REFERENCE TO RELATED APPLICATIONS

This application claims priority to European Patent Application No. 13002919.2 filed Jun. 6, 2013, the disclosure of which is incorporated herein by reference.

BACKGROUND OF THE INVENTION

The present disclosure generally relates to a bending instrument for bending surgical elements such as bone plates for the craniomaxillofacial region. In particular, a bending instrument for surgical elements and a system comprising the bending instrument and a surgical element are described.

As a preliminary to or during a surgical intervention it is often necessary to adapt and match implants and other surgical elements to anatomical circumstances. The anatomical circumstances can be determined for example by the curvature of a bone or the course of a fracture. In order to adapt surgical elements to anatomical circumstances, the surgeon has a wide range of instruments at his disposal. This range of instruments includes for example cutting forceps, bending forceps, plate benders and similar instruments.

U.S. Pat. No. 5,651,283 A discloses a device for contouring elongate bone plates. The device comprises an inner handle from which an upper jaw extends, an outer handle and a lower jaw pivotally connected to the upper jaw. The device further comprises two upper arcing anvils extending laterally from the upper jaw and a lower arcing anvil that extends laterally from the lower jaw. By squeezing the outer handle towards the inner handle, the lower jaw swings about its pivot axis towards the upper anvils. In this manner, a bone plate disposed between the two upper anvils and the lower anvil may be bent in the extension plane of the bone plate.

Additionally, the device in U.S. Pat. No. 5,651,283 A comprises a groove formed in the upper jaw and a complementary tongue formed in the lower jaw. By forcibly closing the handles, a plate may be bent in a plane substantially perpendicular to its extension plane by the groove and complementary tongue.

US 2009/0222020 A1 discloses bending forceps for bending bone plates. The bending forceps comprise two rotationally coupled branches, a first bending punch and two first counter bearings. By actuating the branches, an actuating device converts an actuating movement of the branches into a linear movement of the first bending punch in a region between two first counter bearings. In this manner, a bone plate disposed between the first bending punch and the first counter bearings may be bent in the extension plane of the bone plate. In US 2009/0222020 A1, each of the first counter bearings has a droplet shape in order to engage a tapered region of a bone plate.

The bending forceps in US 2009/0222020 A1 additionally comprise a second bending punch and two second counter bearings each formed on one end of the branches on a remote side from their respective handles. Since the branches are rotationally coupled, actuation of the branches renders the second counter bearings to adapt a circular path about the pivot axis of the branches. In this way, a bone plate disposed between the second counter bearings and the second bending punch may be bent in a plane substantially perpendicular to its extension plane.

BRIEF SUMMARY OF THE INVENTION

There is a need for a bending instrument for surgical elements which has a high bending performance and a simple structure.

According to one aspect, a bending instrument for a surgical element is provided, wherein the bending instrument comprises two branches which are pivotable relative to one another, a bending punch, two counter members for the bending punch, an actuating device for the bending punch, adapted to convert an actuating movement of the branches into a linear movement of the bending punch in a direction towards a region between the two counter members in order to bend the surgical element therebetween, first and second bending structures for co-operatively bending the surgical element, wherein the bending instrument is configured to convert an actuating movement of the branches into a mating movement of the first and second bending structures.

In the present and any further aspect, the branches may be rotationally coupled to each other. Alternatively, one or both of the branches may be rotationally coupled to an intermediate member.

One counter member may be coupled to a first of the two branches and the other counter member may be coupled to the second of the two branches. The two counter members can be fixed immovably relative to one another, or can be variably spaced from one another depending on the actuating state of the branches.

It is possible to provide both counter members on one and the same branch. As an alternative, one or both of the counter members may be provided on an intermediate member with which at least one of the two branches is rotationally coupled.

One possible design of the actuating device includes a gear mechanism for converting the pivotal movement of the branches into the desired linear movement of the bending punch. The gear mechanism can have a gear ratio such that the pivotal movement of the branches results in a comparatively wide axial displacement or misalignment of the bending punch. This axial displacement is for example more than about 1 cm.

The gear mechanism can be a lever mechanism. In this regard, various realisations are conceivable. For example, the actuating device can be designed in the manner of an elliptical linkage gear mechanism. Examples of elliptical linkage gear mechanisms are described in Chapters 3.4.5.7.1 and 3.4.5.7.2 of the handbook by S. Hildebrand, entitled "Feinmechanische Bauelemente", Karl Hanser Verlag, Munich. The described elliptical linkage gear mechanisms and modifications thereof are capable of converting an actuating movement of the branches into a linear bending punch movement. For this purpose the gear mechanism can be articulatedly coupled to each of the two branches as well as to the bending punch.

In one realization of the bending instrument the actuating device (thus for example the elliptical linkage gear mechanism) comprises at least a first lever, which is articulatedly coupled to a first of the two branches and to the bending punch. The actuating device can furthermore include a second lever, which is articulatedly coupled to the second branch and likewise to the bending punch. The first and second levers can be coupled to one another and also to the bending punch by means of a common joint. The common joint is, according to a first variant, formed directly in the region of the bending punch.

According to a second variant the bending punch is spaced apart from the common joint. For this purpose the bending instrument can include an extension arm with two oppositely facing ends. The bending punch is conveniently arranged on a first end of the extension arm, while a second end of the extension arm can be articulatedly coupled to the first and to the second levers. The bending punch can be designed in one piece with the extension arm. Guide means may optionally be provided, which stabilise the linear movement of the bending punch.

The first and second bending structures may have complementary profiles which define a bent shape of the surgical element. For example, the first bending structure may have a concave shape and the second bending structure may have a convex shape.

The first bending structure may be rigidly coupled with a first of the two branches and the second bending structure may be rigidly coupled with a second of the two branches. Alternatively, one or both of the first and second bending structures may be articulatedly coupled with one of the branches.

The mating movement between the first and second bending structures may be accomplished by arranging the first and second bending structures pivotable about a common axis at substantially the same radial distance from the axis. Alternatively, the mating movement between the first and second bending structures may be realized by linearly guiding one or both of the first and second bending structures towards the other.

The bending instrument may be configured to bend a planar surgical element with the bending punch together with the two counter members in an extension plane of the surgical element. Thereby, a portion of the surgical element subjected to bending may maintain a substantially flat appearance.

Alternatively, or in addition, the bending instrument may be configured to bend the planar surgical element with the first and second bending structures in a direction substantially perpendicular to an extension plane of the surgical element. Thereby, the surgical element may obtain a shape that at least partially extends from its original extension plane.

The bending instrument may comprise a linkage for converting the actuating movement of the branches into the mating movement of the first and second bending structures. The linkage may be a parallel linkage. According to one realization, a portion of a first of the branches and a portion of a second of the branches may constitute parts of the parallel linkage. Alternatively, or in addition, the first and second bending structures may be formed on extensions of links in the parallel linkage.

The linkage may comprise a first link member coupled to the first bending structure and rotationally coupled to a first of the two branches, and a second link member coupled to the second bending structure, rotationally coupled to a second of the two branches and rotationally coupled to the first link member.

The first bending structure may comprise a concave profile and the second bending structure may comprise a pointing profile. For example, the pointing profile may adapt the shape of a ridge. The pointing profile may additionally have a circular appearance with an imaginary center axis substantially parallel with an imaginary center axis of the concave profile. The circular appearance of the pointing profile may have a first radius and the concave profile may have a circular appearance with a second radius larger than the first radius.

The second bending structure may comprise a curved ridge extending substantially perpendicular to the direction of the mating movement. In other words, the curved ridge may extend substantially parallel with the center axis of the bending instrument.

The curved ridge may be configured to simultaneously engage two opposite valley regions of a bone plate. The imaginary center axes of the concave profile and the curved ridge may each be substantially perpendicular to each other and to the mating direction.

According to a further aspect, a bending instrument for a surgical element having a plurality of regularly spaced peak regions and a plurality of regularly spaced valley regions is provided, wherein the bending instrument comprises two branches which are pivotable relative to one another, a first counter member comprising a pointing profile adapted to engage a valley region of the surgical element, a second counter member comprising a concave profile adapted to engage a peak region of the surgical element, a bending punch for co-operation with the first and second counter members in order to bend the surgical element therebetween upon engaging a point of the surgical element between said engaged peak region and said engaged valley region, and an actuating device for the bending punch, adapted to convert an actuating movement of the branches into a movement of the bending punch in a direction towards a region between the first and second counter members.

The surgical element may be a bone plate where the peak regions are substantially centered with respect to the valley regions. A peak region may be a region of the surgical element where the width in a direction substantially perpendicular to an extension direction of the surgical element is larger than an average width in a direction substantially perpendicular to an extension direction of the surgical element. A valley region may be a region of the surgical element where the width in a direction substantially perpendicular to an extension direction of the surgical element is smaller than an average width in a direction substantially perpendicular to an extension direction of the surgical element.

The branches, the bending punch and the actuating device of the bending instrument may be configured as described above. For example, the two branches may be rotationally coupled with each other.

The first counter member may be coupled to a first of the two branches and the second counter member may be coupled to the second of the two branches. The two counter members can be variably spaced from one another depending on the actuating state of the bending forceps.

Alternatively, the two counter members can be fixed immovably relative to one another. This can be realized by providing both counter members on one and the same branch. As a further alternative, one or both of the counter members may be provided on an intermediate member with which at least one of the two branches is rotationally coupled.

The first counter member may have a substantially flat shape with an extension substantially in a lateral direction with respect to a branch to which it is coupled. Alternatively, the pointing profile of the first counter member may be constituted by a projection from a more voluminous piece of the first counter member, such as, for example, a cylindrical piece. The pointing profile of the first counter member may have a substantially circular tip portion.

The first counter member may be coupled to one of the two branches such that the pointing profile is substantially aligned with an extension direction of a portion of the branch to which it is coupled. Furthermore, the pointing profile of the first counter member may point in a direction substantially perpendicular to an imaginary line between the pointing profile of the first counter member and the concave profile of the second counter member in a non-actuated state of the bending instrument.

The second counter member may adapt a substantially flat arc shape. Thereby, the inner side of the arc shaped second counter member constitutes the concave profile. Alternatively, the concave profile may be constituted by an aperture in a more voluminous piece of the second counter member, such as, for example, a cylindrical piece.

The concave profile of the second counter member may be substantially circular. Furthermore, the concave profile of the second counter member may face the bending punch in a non-actuated state and/or an actuated state of the bending instrument. The concave profile of the second counter member may have an angular extension of 20 to 170 degrees, for example between 40 and 120 degrees (e.g., 80 degrees). The radius of the circular tip portion of the pointing profile of the first counter member may be smaller than the radius of the concave profile of the second counter member.

The bending instrument may be configured such that upon reaching a certain degree of actuation of the branches, the engaging point of the pointing profile of the first counter member, the engaging point of the bending punch and the engaging point of the concave profile of the second counter member are substantially aligned along a line. In this position, the pointing profile of the first counter member may be inclined with respect to this line with an angle of 50 to 90 degrees, for example between 60 and 80 degrees (e.g., 70 degrees).

The first and/or second counter member may be formed integrally with a branch, for example, through a joint casting process. Alternatively, the first and/or second counter member may be formed as separate pieces with respect to the branches and rigidly coupled thereto.

The thicknesses of the first and second counter members may be 3 to 7 mm, for example 5 mm. The thicknesses of the first and second counter members may be measured in a direction substantially perpendicular to their respective attachment surfaces, for example on the branches. In other words, the thickness of the first counter member may be measured in a direction perpendicular to an extension direction of the pointing profile and the thickness of the second counter member may be measured in a direction substantially parallel to an imaginary center axis of the concave profile.

The bending punch may comprise a pointing profile adapted to engage a valley region of the surgical element. The pointing profile of the bending punch may have a similar shape as the pointing profile of the first counter member.

Alternatively, or in addition, the pointing profile of the bending punch may be U-shaped so as to at least partially enclose an engaged valley region of the surgical element. The U-shape of the pointing profile of the bending punch may have a substantially circular lower portion and an imaginary center axis substantially parallel with a direction between the pointing profile of the first counter member and the concave profile of the second counter member. As an alternative, the pointing profile of the bending punch as described above may be substituted with a concave profile for engaging a peak region of the surgical element.

The pointing profile of the first counter member and the concave profile of the second counter member may be asymmetrically arranged with respect to a center axis of the bending instrument. The concave profile of the second counter member may be arranged closer to the center axis of the bending instrument than the pointing profile of the first counter member. For example, the distance between the pointing profile of the first counter member and the center axis of the bending instrument may be approximately 1.3 times the distance between a mid-portion of the concave profile of the second counter member and the center axis of the bending instrument.

The bending punch may be positioned on the center axis of the bending instrument in a non-actuated state. The center axis of the bending instrument may be defined as an axis centered between the branches. In the case of a pivot connection between the branches, this pivot may be positioned on the center axis of the bending instrument.

The actuating device may be adapted to convert an actuating movement of the branches into a linear movement of the bending punch in a direction towards a region between the first and second counter members. The movement of the bending punch may be in any direction between a direction towards the pointing profile of the first counter member and a direction towards the concave profile of the second counter member. For example, the actuating device may be configured to convert an actuating movement of the branches into a linear movement of the bending punch substantially along the center axis of the bending instrument.

The first counter member may further comprise a concave profile adapted to engage a peak region immediately adjacent the valley region engaged by the pointing profile of the first counter member. A portion of the pointing profile of the first counter member and the concave profile of the first counter member may be the same. The pointing profile of the first counter member and the concave profile of the first counter member may together approximately adapt an S-shape.

The concave profile of the first counter member may have substantially the same curvature as the concave profile of the second counter member. Additionally, the concave profile of the first counter member may have a shorter angular extension in comparison with the concave profile of the second counter member. For example, the angular extension of the concave profile of the first counter member may be 70 degrees. The concave profile of the first counter member may have a circular appearance with a first radius and the pointing profile of the first counter member may have a circular appearance with a second radius smaller than the first radius.

The second counter member may further comprise a pointing profile. The second counter member may be adjustable into a position where the pointing profile is adapted to engage a valley region. The pointing profile of the first counter member and the pointing profile of the second counter member may thereby simultaneously engage two different valley regions of the surgical element. The pointing profile of the second counter member may have a similar shape as the pointing profile of the first counter member.

The adjustment of the second counter member may be a rotational adjustment. This adjustment may be realized by providing a keyed opening in one of the branches and by providing a keyed profile which fits in the keyed opening in two different rotational positions. The second counter member may be secured in one of the two different rotational positions by being biased towards the branch, for example by means of a spring.

The second counter member may be rotationally positioned such that the pointing profile of the second counter member is symmetrically arranged with the pointing profile of the first counter member with respect to the center axis of the bending instrument.

According to a further aspect, there is provided a system comprising the bending instrument as described above and a surgical element having a plurality of regularly spaced peak regions and a plurality of regularly spaced valley regions. The surgical element may have a thickness of between 1 and 8 mm, for example between 2 and 5 mm (e.g., 2.5 mm). The thickness may be regarded as the dimension of the surgical element in a direction substantially perpendicular to its extension plane.

The surgical element may further have a plurality of screw holes for securing the surgical element to bone (e.g., with bone screws). The screw holes may be through holes and extend in a direction substantially perpendicular to the extension plane of the surgical element. Furthermore, the screw holes may each be substantially concentric with a peak region. The screw holes may be countersunk in order to receive a head of a bone screw. The surgical element may have a substantially linear appearance (e.g., the centers of the screw holes may be arranged on a straight or curved line).

A distance between the pointing profile of the first counter member and the concave profile of the second counter member in a non-actuated state of the bending instrument may correspond to a distance between a peak region and a valley region. The concave profile of the second counter member may substantially correspond to at least one of the peak regions.

BRIEF DESCRIPTION OF THE DRAWINGS

Further details, advantages and aspects of the present disclosure will become ap-parent from the following embodiments taken in conjunction with the drawings, wherein.

DETAILED DESCRIPTION

Figure 1:
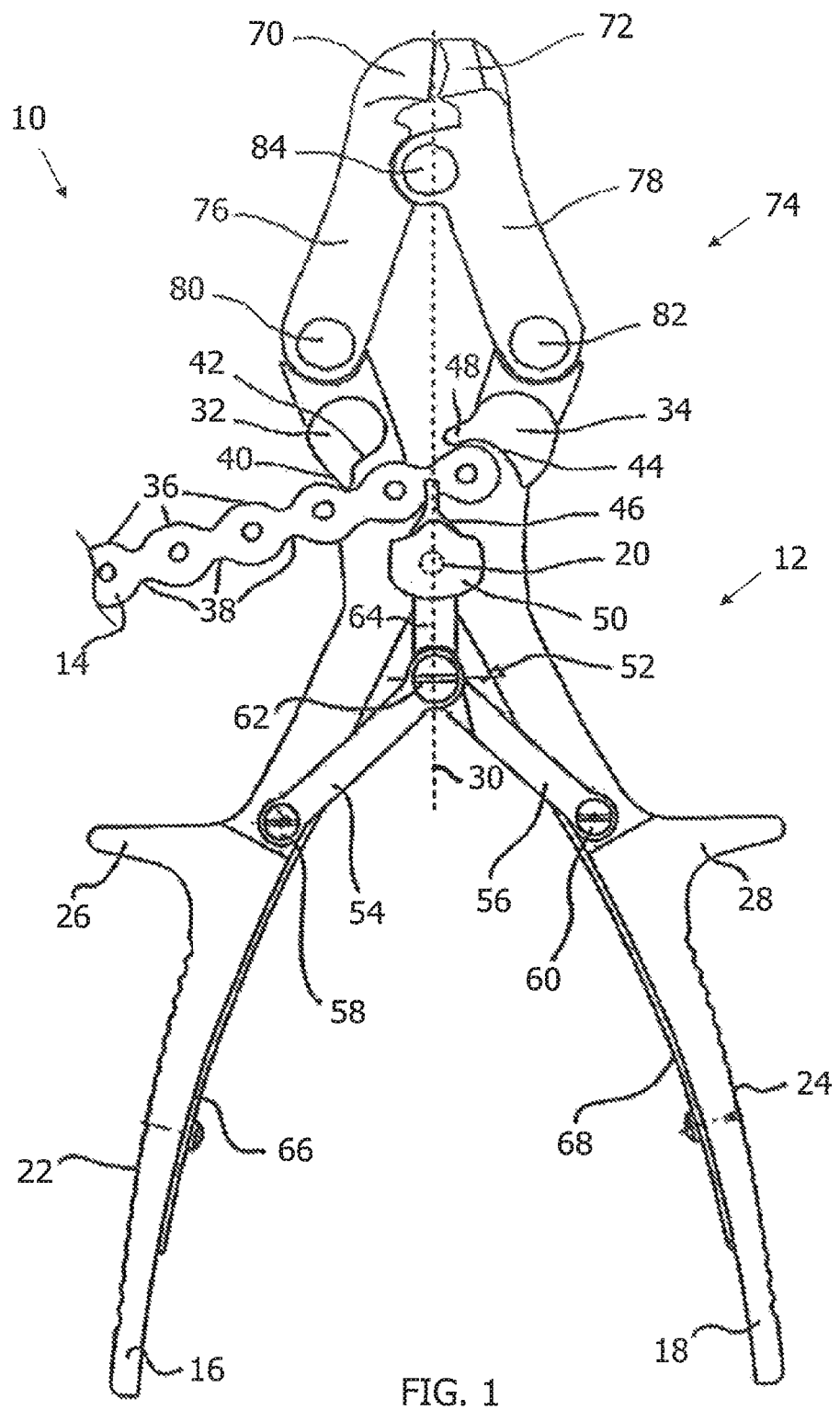
FIG. 1 shows a plan view of a system embodiment comprising a bending instrument in a non-actuated position and a surgical element.

In the following, embodiments of a bending instrument for surgical elements will be described. The same reference numerals will be used to denote the same or similar structural features.

FIG. 1 shows a plan view of a system 10 comprising a bending instrument 12 in a non-actuated position and a surgical element 14. In this view, the bending instrument 12 is in a non-actuated position. The bending instrument 12 has two branches 16, 18.

The two branches 16, 18 can in this embodiment pivot about a common axis of rotation, which in FIG. 1 is defined by a rotation bearing 20 (which is not visible in the plan view). The lower ends of the two branches 16, 18 in FIG. 1 are designed as handles 22, 24. The handles 22, 24 have each a structured surface and an outwardly extending projection 26, 28. A center axis 30 is centered with respect to the branches 16, 18. In this configuration, the center axis 30 also passes through the rotation bearing 20.

The two projections 26, 28 facilitate the manipulation of the bending instrument 12 and, just like the structured surfaces, prevent a surgeon's hand slipping in the direction of the bone plate to be bent. The danger of a hand slipping off exists in particular when great actuation forces are necessary in the case of thick bone plates.

An end of the bending instrument 12 in the region of the handles 22, 24 (lower end in FIG. 1) is in the following referred to as a proximal end. Moreover, an end opposite to the proximal end (upper end in FIG. 1) is referred to as a distal end. Consequently, a proximal direction and a distal direction are defined in a corresponding manner.

Each of the two branches 16, 18 has a bent shape in the region of the rotation bearing 20. In other words, each of the two branches 16, 18 is bent away from the rotation bearing 20. The portions of the branches 16, 18 distal from the rotation bearing 20 are each inclined with respect to the center axis 30 by approximately 30 degrees. Similarly, the portions of the branches 16, 18 proximal from the rotation bearing 20 are each inclined with respect to the center axis 30 by approximately 30 degrees. Thereby, the two branches 16, 18 together approximately constitute an X-shape.

At a distal portion of the first branch 16, a first counter member 32 is provided. Similarly, at a distal portion of the second branch 18, a second counter member 34 is provided. The first and second counter members 32, 34 are each rigidly attached to a surface of the first branch 16 and a surface of the second branch 18, respectively. Thereby, the first and second counter members 32, 34 are variably spaced from one another depending on the actuating state of the branches 16, 18.

The first and second counter members 32, 34 extend outwardly from the plane of the drawing in FIG. 1. The first and second counter members 32, 34 also protrude outwardly from substantially flat surfaces of distal portions of the branches 16, 18.

The distances of the two counter members 32, 34 from the rotation bearing 20 are shorter than the distance of the two handles 22, 24 from the rotation bearing 20. The resulting leverage ratios reduce the force required to bend a surgical element 14.

In FIG. 1, a surgical element 14 in the form of a substantially linear bone plate can be seen. The surgical element 14 has a thickness of ca. 2.5 mm and an extension plane substantially aligned with the plane of FIG. 1. The surgical element 14 has a plurality of regularly spaced peak regions 36 and a plurality of regularly spaced valley regions 38. A plurality of screw holes are provided in the surgical element 14. Each screw hole is substantially concentric with a peak region 36.

As can be seen in FIG. 1, the peak regions 36 are regions of the surgical element 14 where the width in a direction substantially perpendicular to the extension direction of the surgical element 14 is larger than an average width in a direction substantially perpendicular to an extension direction of the surgical element 14. Similarly, the valley regions 38 are regions of the surgical element 14 where the width in a direction substantially perpendicular to an extension direction of the surgical element 14 is smaller than an average width in a direction substantially perpendicular to an extension direction of the surgical element 14. The peak regions 36 are substantially centered with respect to the valley regions 38.

In the position of FIG. 1, a substantially flat rear side of the surgical element 14 is supported by substantially flat surfaces at distal regions of both branches 16, 18. Thereby, these flat surfaces of the branches 16, 18 constitute support surfaces for the surgical element 14.

The first counter member 32 comprises a convex, or pointing profile 40. In the illustrated position in FIG. 1, the pointing profile 40 points towards a valley region 38 of the surgical element 14. The pointing profile 40 comprises two substantially flat opposite surfaces which are inclined with respect to each other and joined by a substantially circular tip portion. The inclination angle between the two opposite surfaces of the pointing profile 40 is approximately 60 degrees. Thereby, the inclination angle of the pointing profile 40 is somewhat sharper than the inclination angle of the valley regions 38 of the surgical element 14.

The first counter member 32 also comprises a substantially cylindrical piece from which the pointing profile 40 projects. This cylindrical piece has a flat surface substantially parallel with a surface of the distal portion of the branch 16 to which the first counter member 32 is coupled.

The first counter member 32 is coupled to the branch 16 such that the pointing profile 40 is substantially aligned with an extension direction of a portion of the branch 16 to which it is coupled. In the illustrated non-actuated configuration of the bending instrument 12 in FIG. 1, the pointing profile 40 is inclined approximately 30 degrees with respect to the center axis 30.

The first counter member 32 further comprises a concave profile 42 for engaging a peak region 36 of the surgical element 14. The concave profile 42 is arranged adjacent the pointing profile 40 along the circumference of the first counter member 32. Thereby, the concave profile 42 is adapted to engage a peak region 36 immediately adjacent a valley region 38 engaged by the pointing profile 40.

A portion of the pointing profile 40 and the concave profile 42 of the first counter member 32 are the same. That is, the concave profile 42 is constituted by a substantially straight portion of the pointing profile 40 and a substantially circular portion. Alternatively, the straight portion of the pointing profile 40 facing the center axis 30 may be also be substantially circular. Thereby, the pointing profile 40 and the concave profile 42 of the first counter member 32 together adapt an S-shape.

The angular extension of the concave profile 42 of the first counter member 32 is approximately 70 degrees. As can be seen in FIG. 1, the concave profile 42 has a circular appearance with a first radius and the pointing profile 40 has a circular appearance with a second radius smaller than the first radius.

The second counter member 34 comprises a concave profile 44. The concave profile 44 is substantially circular. The angular extension of the concave profile 44 is approximately 80 degrees. Thus, in this embodiment, the angular extension of the concave profile 44 of the second counter member 34 is slightly larger than the angular extension of the concave profile 42 of the first counter member 32.

In the illustrated position in FIG. 1, the concave profile 44 engages a peak region 36 of the surgical element 14. Additionally, the concave profile 44 circumferentially encloses an end portion of the surgical element 14. This end portion of the surgical element 14 has a substantially circular edge joining two opposite peak regions 36.

The concave profile 44 faces a bending punch 46 (described later) in the non-actuated state of the bending instrument 12. Also in the non-actuated state of the bending instrument 12, the pointing profile 40 of the first counter member 32 points in a direction substantially perpendicular to an imaginary line between the pointing profile 40 of the first counter member 32 and the concave profile 44 of the second counter member 34.

The concave profile 44 is constituted as an aperture in a roughly cylindrical piece. This cylindrical piece has a flat surface substantially aligned with a surface of the branch 18 to which the second counter member 34 is coupled.

As can be seen in FIG. 1, the radius of the concave profile 44 is slightly larger than the radius of the end portion and the peak regions 36 of the surgical element 14. However, the concave profile 44 may have a radius which substantially corresponds to the radius of the end portion and the peak regions 36 of the surgical element 14.

The radius of the concave profile 44 of the second counter member 34 is substantially equal to the concave profile 42 of the first counter member 32. Consequently, also the radius of the concave profile 44 of the second counter member 34 is larger than the radius of the circular tip portion of the pointing profile 40 of the first counter member 32.

In FIG. 1, the pointing profile 40 of the first counter member 32 and the concave profile 44 of the second counter member 34 are asymmetrically arranged with respect to the center axis 30 of the bending instrument 12. The concave profile 44 of the second counter member 34 is arranged closer to the center axis 30 of the bending instrument 12 than the pointing profile 40 of the first counter member 32.

In the illustrated configuration, the distance between the pointing profile 40 of the first counter member 32 and the center axis 30 of the bending instrument 12 is approximately 1.3 times the distance between a mid-portion of the concave profile 44 of the second counter member 34 and the center axis 30 of the bending instrument 12. Thus, in the illustrated non-actuated state of the bending instrument 12, the distance between the pointing profile 40 of the first counter member 32 and the concave profile 44 of the second counter member 34 substantially corresponds to approximately 3 times (e.g., approximately 2.25 to 3.75 or 2.5 to 3.5 times) a distance between a valley region 38 and the immediately adjacent peak region 36 of the surgical element 14.

The distance between the pointing profile 40 of the first counter member 32 and the center axis 30 of the bending instrument 12 may generally be selected as "n*L", where n denotes an integer and L denotes a periodic length of the surgical element 14, such as a distance between two adjacent peak regions 36. Moreover, the distance between a mid-portion of the concave profile 44 of the second counter member 34 and the center axis 30 of the bending instrument 12 may be selected as "n*L−0.25*L". A mid-portion of the concave profile 44 is referred to as a center point along its circumferential extension.

The second counter member 34 further comprises a pointing profile 48. If desired, the second counter member 34 may be adjustable into a position where the pointing profile 48 is adapted to engage a valley region 38. The pointing profile 40 of the first counter member 32 and the pointing profile 48 of the second counter member 34 may thereby simultaneously engage two different valley regions 38 of the surgical element 14.

The pointing profile 48 of the second counter member 34 has a similar shape as the pointing profile 40 of the first counter member 32. In FIG. 1, the pointing profile of the second counter member 34 is substantially perpendicular to the pointing profile 40 of the first counter member 32.

A bending punch 46 is provided in a region between the two counter members 32, 34 and slightly spaced apart from the two counter members 32, 34 along the center axis 30 of the bending instrument 12. In FIG. 1, the bending punch 46 is covered by a linear guide 50 for the bending punch 46.

The bending punch 46 has a convex, or pointing profile adapted to engage a valley region 38 of the surgical element 14. The bending punch 46 is further U-shaped and thereby partially encloses an engaged valley region 38 of the surgical element 14, as can be seen in FIG. 1. Thus, the lower portion of the U-shape of the bending punch 46 has a convex or pointing profile. The U-shape of the bending punch 46 has an imaginary center axis substantially parallel with a direction between the two counter members 32, 34, i.e., substantially perpendicular to the center axis 30 of the bending instrument 12.

An actuating device 52 is provided for the bending punch 46. The actuating device 52 converts an actuating movement of the two branches 16, 18 into a linear movement of the bending punch 46 in the direction along the center axis 30 of the bending instrument 12. Thus, the actuating device 52 converts an actuating movement of the branches 16, 18 into a linear movement of the bending punch 46 in a direction towards a region between the first and second counter members 32, 34.

The actuating device 52 is designed in the embodiment in the manner of an elliptical linkage gear mechanism, though in contrast to "conventional" elliptical linkage gear mechanisms (cf. the above-mentioned handbook by S. Hildebrand), in the embodiment no fixed anchorage point is provided. The elliptical linkage gear mechanism is instead in the present case coupled to each of the two movable branches 16, 18 and to the bending punch 46 to be actuated.

In the embodiment the actuating device 52 designed as an elliptical linkage gear mechanism includes two equally long levers 54, 56. One lever 54 is coupled via a joint 58 to one branch 16, and the other lever 56 is coupled via a further joint 60 to the other branch 18. At their distal ends, the two levers 54, 56 are coupled by means of a common joint 62 to one another as well as to the bending punch 46.

More precisely, the two levers 54, 56 are connected at the common joint 62 to an extension arm 64 carrying the bending punch 46. In the present case the bending punch 46 is formed in one part with the extension arm 64. With an actuating movement of the two branches 16, 18 the extension arm 64 slides along the linear guide 50, so that the linear guide 50 has a stabilising action on the movement of the extension arm 64 and thus also has a stabilising action on the movement of the bending punch 46.

FIG. 1 shows the initial or normal position of the bending instrument 12. In this position the two handles 22, 24 are held apart from one another by leaf springs 66, 68, which are only partly shown in FIG. 1. When actuating the bending instrument 12 the initial tension of the leaf springs 66, 68 consequently has to be overcome.

In order to bend the surgical element 14 in its extension plane, in a first step the surgical element 14 is, as illustrated in FIG. 1, placed flat on the front surfaces of the distal regions of the branches 16, 18. More particularly, the surgical element 14 is placed in an intermediate space between the bending punch 46 on the one hand and the two counter members 32, 34.

When placing the surgical element 14, this is positioned by the surgeon so that an end portion or a peak region 36 of the surgical element 14 abuts against the concave profile 44 of the second counter member 34 and so that the pointing profile 40 of the first counter member 32 abuts against a valley region 38 of the surgical element 14. In order to achieve this, the surgical element 14 may be slid in its extension direction until it abuts against the concave profile 44. Subsequently, the surgical element 14 may be slightly rotated (clockwise in FIG. 1) with this contact point maintained until the pointing profile 40 abuts against the valley region 38.

In case the pointing profile 40 is not properly aligned with a valley region 38 of the surgical element 14, the surgical element 14 may be held abutting against the concave profile 44 while slightly closing the branches 16, 18 until the pointing profile 40 is aligned with respect to a valley region 38. Thus, the surgical element 14 can be precisely positioned before initiating a bending operation due to the pointing profile 40 and the concave profile 44.

A movement of the branches 16, 18 towards one another then takes place by actuating the branches 16, 18, while overcoming the initial tension of the leaf springs 66, 68. The actuating movement of the branches 16, 18 is converted by the actuating device 52 into a linear movement of the bending punch 46 along the center axis 30 of the bending instrument 12. This conversion is due to the fact that the two levers 54, 56 approach one another. As a consequence of this approach movement, the common joint 62 of the two levers 54, 56 and thus also of the extension arm 64 for the bending punch 46 coupled to this joint 62, is moved along the center axis 30 of the bending instrument 12. Thereby, a valley region 38 of the surgical element 14 is engaged by the bending punch 46.

Upon further actuation of the branches 16, 18, the surgical element 14 is bent in its extension plane (i.e., "in-plane") while maintaining the contacts between the pointing profile 40 and a valley region 38 and between the linearly moving bending punch 46 and a valley region 38. During the bending operation, the contact point between the concave profile 44 and the surgical element 14 may in one implementation be allowed to move along the concave profile 44. For example, an initial contact point may be between an end portion of the surgical element 14 along its extension direction and a lower point on the concave profile 44. As the bending progresses, the contact is allowed to progressively shift to a contact point between a peak region 36 of the surgical element 14 and a higher point on the concave profile 44 as the counter members 32, 34 move apart from each other. In other words, the contact may then be shifted in a counter-clockwise direction along the concave profile 44 in FIG. 1.

Due to the profiles 40, 44 of the counter members 32, 34, the surgical element 14 can be bent in a region close to its end around the bending punch 46. More precisely, the surgical element 14 can be bent about its last valley region 38 due to the engagement of the last valley region 38 with the bending punch 46, the engagement of the last peak region 36 with the concave profile 44 and the engagement of the penultimate valley region 38 with the pointing profile 40. This improves the precision of the bending performance.

The bending instrument 12 further comprises a first bending structure 70 and a second bending structure 72 for co-operatively bending the surgical element 14. The first and second bending structures 70, 72 are provided at a distal end of the bending instrument 12.

The first bending structure 70 has a concave shape with an imaginary center axis substantially parallel with the center axis 30 of the bending instrument 12 in the position of FIG. 1. The second bending structure 72 has a convex shape which is substantially complementary with the concave shape of the first bending structure 70.

In the configuration illustrated in FIG. 1, the first and second bending structures 70, 72 are configured so as to bend the surgical element 14 in a direction substantially perpendicular to its extension plane (i.e., "out-of-plane"). For example, the surgical element 14 may be bent about an imaginary axis between two corresponding peak regions 36 in this way. Thereby, the surgical element 14 may adapt a profile having more than one extension plane.

A linkage 74 is provided in a distal region of the bending instrument 12 between the two handles 22, 24 and the two bending structures 70, 72. The linkage 74 comprises a first link member 76 and a second link member 78. The first link member 76 is rotationally coupled to a distal portion of the first branch 16 via a joint 80. Similarly, the second link member 78 is rotationally coupled to a distal portion of the second branch 18 via a joint 82. Furthermore, the first link member 76 is rotationally coupled to the second link member 78 via a joint 84. Thus, the first and second bending structures 70, 72 are articulatedly coupled with the first and second branch 16, 18, respectively.

In the embodiment of FIG. 1, the first and second link members 76, 78 are each constituted by a common piece as the first and second bending structures 70, 72, respectively. The joint 84 is provided between the first bending structure 70 and the joint 80 and between the second bending structure 72 and the joint 82, respectively.

Upon actuating the handles 22, 24 toward each other, the branches 16, 18 pivot about the rotation bearing 20. Thereby, the joints 80, 82 move apart from each other along circular paths about the rotation bearing 20. At the same time, the angle between the first and second link members 76, 78 becomes more flattened. As a consequence, the joint 84 adapts a movement along the center axis 30 of the bending instrument 12 in a direction towards the rotation bearing 20.

This relative inclination of the first and second link members 76, 78 renders the first and second bending structures 70, 72 to approach each other along circular (or, generally, elliptical) paths about the joint 84. In this manner, a mating movement between the first and second bending structures 70, 72 is realized since the first and second bending structures 70, 72 are arranged substantially at the same radial distance from the joint 84. Thus, the linkage 74 converts an actuating movement of the branches 16, 18 into a mating movement of the first and second bending structures 70, 72.

In FIG. 1, the first link member 76 between the joints 80, 84, the second link member 78 between the joints 82, 84, a portion of the branch 16 between the joint 80 and the rotation bearing 20 and a portion of the branch 18 between the joint 82 and the rotation bearing 20 constitute a parallel linkage.

The first bending structure 70 comprises a concave profile. More particularly, the first bending structure 70 comprises a substantially circular profile with an imaginary center axis substantially parallel with the center axis 30 of the bending instrument 12. The second bending structure 72 comprises a pointing profile. The pointing profile is in this embodiment a ridge which extends substantially parallel with the center axis 30 of the bending instrument 12.

The ridge of the second bending structure 72 additionally has a circular appearance with a first radius and the concave profile of the first bending structure 70 has a circular appearance with a second radius larger than the first radius.

In the embodiment of FIG. 1, the ridge of the second bending structure 72 is slightly curved. The curved ridge is thereby configured to simultaneously engage two opposite valley regions 38 of the surgical element 14. The curved ridge extends substantially parallel with the center axis 30 of the bending instrument 12.

Figure 2:
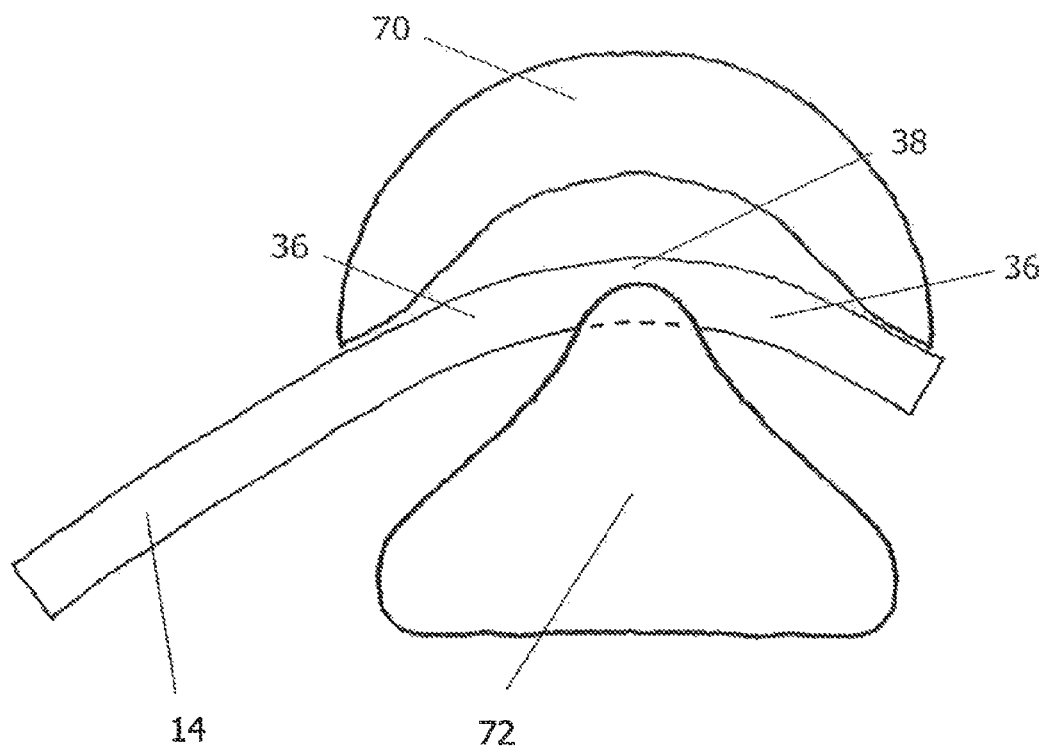
FIG. 2 shows a top view of a first and second bending structure and a surgical element according to the embodiment of FIG. 1.

FIG. 2 shows a top view of the first and second bending structures 70, 72 and the surgical element 14 disposed therebetween during a bending operation. FIG. 2 is a view along the center axis 30 from the distal end of the surgical instrument 12. However, the remaining parts of the surgical instrument 12 are omitted in this view.

In the position of FIG. 2, the curved ridge of the second bending structure 72 engages two opposite valley regions 38 (only one valley region 38 can be seen). At the same time, end portions of the first bending structure 70 engage portions of the surgical element 14 slightly outwardly from the two peak regions 36 adjacent the valley region 38. Upon further mating movement between the first and second bending structures 70, 72, the surgical element 14 is pushed by the second bending structure 72 against a mid-portion of the concave profile of the first bending structure 70. Thereby, the surgical element 14 is forced to adapt a profile substantially corresponding to the concave profile of the first bending structure 70.

Thus, in order to bend the surgical element 14 in a plane substantially perpendicular to its extension plane, the surgical element 14 can be inserted between the first and second bending structures 70, 72 with its extension direction oriented substantially perpendicular to the center axis 30 of the bending instrument 12 and with its extension plane oriented substantially parallel with the center axis 30 of the bending instrument 12. The surgical element 14 can be aligned in its extension direction by engaging two opposite valley regions 38 with the curved ridge.

Subsequently, the branches 16, 18 are actuated to press the surgical element 14 inserted between the first and second bending structures 70, 72 in order to bend the surgical element 14. During this actuation, the movement of the two bending structures 70, 72 has a substantially linear relationship with the movement of the branches 12, 14.

While the present disclosure has been described with reference to an exemplary embodiment, it will be appreciated that the present invention is not limited to what has been described above. For example, it will be appreciated that the dimensions of the parts may be varied as needed. Accordingly, it is intended that the present invention may be limited only by the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bending instrument for a surgical element, comprising
    two branches which are pivotable relative to one another;
    a bending punch;
    first and second counter members for the bending punch;
    an actuating device for the bending punch, adapted to convert an actuating movement of the branches into a linear movement of the bending punch in a direction towards a region between the first and second counter members in order to bend the surgical element therebetween;
    first and second bending structures for co-operatively bending the surgical element;
    wherein the bending instrument is configured to convert an actuating movement of the branches into a mating movement of the first and second bending structures.

2. The bending instrument according to claim 1, wherein the bending instrument is configured to bend a planar surgical element with the bending punch together with the two counter members in an extension plane of the surgical element.

3. The bending instrument according to claim 1, wherein the bending instrument is configured to bend the planar surgical element with the first and second bending structures in a direction substantially perpendicular to an extension plane of the surgical element.

4. The bending instrument according to claim 1, further comprising a linkage for converting the actuating movement of the branches into the mating movement of the first and second bending structures.

5. The bending instrument according to claim 4, wherein the linkage is a parallel linkage.

6. The bending instrument according to claim 4, wherein the linkage comprises
a first link member coupled to the first bending structure and rotationally coupled to a first of the two branches, and
a second link member coupled to the second bending structure, rotationally coupled to a second of the two branches and rotationally coupled to the first link member.

7. The bending instrument according to claim 1, wherein the first bending structure comprises a concave profile and the second bending structure comprises a pointing profile.

8. The bending instrument according to claim 1, wherein the second bending structure comprises a curved ridge extending substantially perpendicular to the direction of the mating movement.

9. A bending instrument for a surgical element having a plurality of regularly spaced peak regions and a plurality of regularly spaced valley regions, wherein the bending instrument comprises:
two branches which are pivotable relative to one another;
a first counter member comprising a pointing profile adapted to engage a valley region of the surgical element;
a second counter member comprising a concave profile adapted to engage a peak region of the surgical element
a bending punch for co-operation with the first and second counter members in order to bend the surgical element therebetween upon engaging a point of the surgical element between said engaged peak region and said engaged valley region; and
an actuating device for the bending punch, adapted to convert an actuating movement of the branches into a movement of the bending punch in a direction towards a region between the first and second counter members.

10. The bending instrument according to claim 9, wherein the bending punch comprises a pointing profile adapted to engage a valley region.

11. The bending instrument according to claim 9, wherein the pointing profile of the first counter member and the concave profile of the second counter member are asymmetrically arranged with respect to a center axis of the bending instrument.

12. The bending instrument according to claim 9, wherein the first counter member further comprises a concave profile adapted to engage a peak region immediately adjacent the valley region engaged by the pointing profile of the first counter member.

13. The bending instrument according to claim 9, wherein the second counter member further comprises a pointing profile and wherein the second counter member is adjustable into a position where the pointing profile is adapted to engage a valley region.

14. The system according to claim 9 further comprising a surgical element having a plurality of regularly spaced peak regions and a plurality of regularly spaced valley regions.

15. The system according to claim 14, wherein a distance between the pointing profile of the first counter member and the concave profile of the second counter member in a non-actuated state of the bending instrument corresponds to a distance between a peak region and a valley region of the surgical element.

16. The system according to claim 9 further comprising a surgical element having a plurality of regularly spaced peak regions and a plurality of regularly spaced valley regions, wherein the concave profile of the second counter member substantially corresponds to at least one of the peak regions of the surgical element.

17. A bending instrument for an axially extending bone plate, having a plurality of spaced peak regions and a plurality of spaced valley regions, wherein the bending instrument comprises:
first and second arms which are pivotable relative to one another, the first arm having a first counter member thereon comprising a pointed profile adapted to engage one valley region of the surgical element;
the second arm having a second counter member thereon comprising a concave profile adapted to engage one peak region of the surgical element;
a first linkage system having a first link pivotally connected to the first arm and a second link pivotally connected to the second arm;
a bending punch connected to the first and second links for co-operation with the first and second counter members moveable by the first linkage system in order to bend the surgical element therebetween upon engaging a point of the surgical element between the engaged peak region and the engaged valley region;
the first linkage system adapted to convert an actuating movement of the branches into a movement of the bending punch in a direction towards a region between the first and second counter members;
a second linkage system having a third link pivotally connected to the first arm and a fourth link pivotally connected to the second arm, the third and fourth links being pivotally connected to each other; and
a first bending structure connected to the third link of the second linkage system and a second bending structure connected to the fourth link of the second linkage system.

18. The system as set forth in claim 17 wherein the first and second arms have a first gripping end and a second end wherein the second linkage system is connected to the first and second arms adjacent the second ends thereof.

19. The system as set forth in claim 17 wherein the second linkage system is capable of producing movement of the first and second bending structures thereon in a direction perpendicular to a longitudinal axis of the bone plate.

20. The system as set forth in claim 19 wherein the first linkage system is an elliptical linkage.

* * * * *